United States Patent [19]

Palm

[11] Patent Number: 4,926,913
[45] Date of Patent: May 22, 1990

[54] METHOD AND A DEVICE FOR ASEPTIC TRANSFER OF AN AMOUNT OF LIQUID FROM ONE SPACE TO ANOTHER

[75] Inventor: Bengt Palm, Genarp, Sweden

[73] Assignee: Alfa-Laval Food & Dairy Engineering AB, Tumba, Sweden

[21] Appl. No.: 295,604

[22] PCT Filed: Jun. 29, 1987

[86] PCT No.: PCT/SE87/00307
§ 371 Date: Dec. 29, 1988
§ 102(e) Date: Dec. 29, 1988

[87] PCT Pub. No.: WO88/00234
PCT Pub. Date: Jan. 14, 1988

[30] Foreign Application Priority Data
Jul. 4, 1986 [SE] Sweden ............... 8602973

[51] Int. Cl.$^5$ ............... B65B 3/04; B65B 31/00
[52] U.S. Cl. ............... 141/1; 141/5; 141/47; 141/51; 141/89; 53/426; 53/468; 222/373
[58] Field of Search ............... 222/373; 53/407, 426, 53/468; 141/1, 4, 5, 11, 39, 47, 48, 49, 50, 51, 63, 69, 82, 89, 91

[56] References Cited

U.S. PATENT DOCUMENTS

| | | | |
|---|---|---|---|
| 3,972,153 | 8/1976 | Kiellarson et al. | 53/426 |
| 4,308,900 | 1/1982 | Vadas | 141/1 |
| 4,458,734 | 7/1984 | Scholle et al. | 141/5 |
| 4,494,363 | 1/1985 | Rica et al. | 53/426 |
| 4,498,508 | 2/1985 | Scholle et al. | 141/5 |
| 4,805,378 | 2/1989 | Anderson | 53/426 |

FOREIGN PATENT DOCUMENTS

| | | |
|---|---|---|
| 2614542 | 11/1977 | Fed. Rep. of Germany . |
| 356682 | 6/1973 | Sweden . |
| 922006 | 9/1980 | U.S.S.R. . |

Primary Examiner—Ernest G. Cusick
Attorney, Agent, or Firm—Davis Hoxie Faithfull & Hapgood

[57] ABSTRACT

Liquid under a given temperature and pressure is aseptically tranferred from a first space to a second space by introducing a gas having a condensation temperature which at the given pressure is higher than the temperature of the liquid, into the second space, permitting the gas to contact the liquid in the first space where it is condensed by contact with the liquid, the lowered pressure in the second space inducing liquid from the first space to flow into the second space.

6 Claims, 2 Drawing Sheets

METHOD AND A DEVICE FOR ASEPTIC TRANSFER OF AN AMOUNT OF LIQUID FROM ONE SPACE TO ANOTHER

FIELD OF THE INVENTION

The present invention relates to a method of aseptic transfer of a sample batch of liquid from a first closed space, which contains such a liquid under a given pressure, to a second space. The invention also relates to a sampling device for accomplishing this method.

BACKGROUND OF THE INVENTION

In a known process for the production of sterilized and packed liquid food, for instance berry juice, cream, sauce, soup, etc., the food is first sterilized in a sterilizer, after which it is conveyed in conduits to an aseptic packing machine, if necessary via an aseptic intermediate storing container. During the process, the sterility of the food must be confirmed by regularly testing the bacterial content of the food. One way of accomplishing such tests is by testing samples of the contents of the filled packages. Another way is to draw off minor quantities of food for testing via valves, which can be arranged at different places along the process line. The latter method is applied in practice by keeping an open container in the vicinity of a valve, while the latter is opened for a short period of time. Usually there is an arrangement which creates an approximately sterile environment around the valve.

A drawback with the first way of testing is that when packages with unsterile content are discovered, it is impossible to directly state where in the process defects have arisen. Locating faults will therefore be time-consuming and expensive. A drawback with the latter method is that the valves often mechanically affect the quantity of food drawn off in an undesirable way. Often the food contains delicate coarse particles such as whole berries, beans, carrots in the form of cubes etc. At times these particles partly clog an open valve, so that the food is filtered when passing through the valve. Of course, also such coarse particles should be included in the sterility test. However, if a valve is opened sufficiently to permit passage of the coarse particles the flow of food through the valve into the relatively small open receptacle normally used can be unacceptably great, since the liquid food is under a certain overpressure in the process apparatus. In certain cases the particles can be mashed when passing through the valve, which means a change of the consistency of the food. Test samples obtained through valves therefore are often not completely representative of the food in the process apparatus. Further, it is difficult to accomplish sampling of food via valves during aseptic conditions. Thus, the samples can be infected by bacteria during the sampling, which of course will give a wrong indication of the condition of the food treated in the process.

The object of the present invention is to avoid the above described drawbacks with the known ways of testing the bacteria content of sterilized liquid food by providing a new method, which admits aseptic transfer of a sample of a limited quantity of food from an optional place in a process apparatus to a sampling receptacle without the food being changed and which in addition admits aseptic transfer of relatively coarse particles in the food to the sampling receptacle. A further object of the present invention is to provide a simple sampling device for accomplishing such a method.

SUMMARY OF THE INVENTION

These objects are obtained according to the invention in a method of the kind initially mentioned, for transferring liquid from a first space having a given pressure to a second space, by filling the second space with a sterile gas such that the pressure in this second space at least amounts to substantially said given pressure in the first space, the gas having a condensation temperature, which at said given pressure is higher than the temperature of the liquid; that after the gas filling of the second space this is brought to communicate with the first space, such that the gas in the second space is condensed by contact with the liquid in the first space, whereby liquid is brought to stream from the first space to the second space; and that the communication between the first and second spaces then is interrupted, so that the liquid in the second space is separated from remaining liquid in the first space.

By this method the advantage is obtained, thanks to the gas pressure in the second space, that communication between the first and second spaces can be established, for instance by opening a valve in a connection channel between the spaces, without the liquid in the first space immediately streaming into the second space. Thus, there is time for complete opening of the valve before liquid starts to flow through it. Consequently, clogging of the valve by coarse particles can be avoided as can the division of coarse particles into pieces when streaming through the valve before it is completely opened. It will also be possible to utilize a valve of such a size that the coarse particles easily can pass through it when it is completely opened, since condensation of the gas takes place very slowly in the beginning after opening of the valve, to increase later as heat exchange contact between the liquid and the gas is established. Therefore, there is time for complete opening of the valve while the liquid flow into the second space still is of a marginal rate.

The invention also relates to a sampling device for aseptic transfer of a batch of liquid from a first space, which contains such liquid under a given pressure, to a second space, said second space being adapted to take up the entire said batch of liquid to be transferred, said sampling device comprising a channel for liquid, which connects the first space with the second space, and a valve adapted for opening and closing of the liquid channel. The sampling device according to the invention is principally characterized by a source for production of a sterile gas at a pressure, which at least amounts to substantially said given pressure, and having a condensation temperature which at said given pressure is higher than the temperature of the liquid; a channel for gas, which connects the second space with the gas source; and a gas valve adapted for opening and closing the gas channel.

Thus the invention provides a simple sampling device is obtained for accomplishing the above described method.

Advantageously, the gas channel opens in the liquid channel in the vicinity of the liquid valve between the liquid channel and the second space. After sampling has been accomplished, the gas can be utilized for cleaning of the outlet portion of the liquid valve and the part of the liquid channel, which is situated between the liquid valve and the second space.

According to a preferred embodiment of the sampling device according to the invention the second space is provided with an outlet, and a valve is adapted for opening and closing of the outlet. Thus, the second space functions as a lock for the liquid, so that the sampling receptacles for the liquid can be of a simple and cheap kind, for instance of glass, since these do not need to resist the pressure variations or sudden temperature changes, which occur in the second space during transfer of liquid from the first space to the second space which is heated by gas. The second space may for instance be constituted by the interior of a pressure vessel of metal, which is resistant to said pressure variations and sudden temperature changes.

Because the second space functions as a lock for the liquid, the emptying of the second space can easily be controlled, so that the liquid flow from this through the outlet will have a desired suitable size when filling a sampling receptacle. In emptying the second space the outlet valve is completely opened while the liquid valve is closed. By supplying gas to the second space the liquid can discharge through the outlet. Thus the size of the liquid flow is adjusted by adjusting the size of the gas flow. Suitably the second space is dimensioned such that this can be completely emptied of the liquid quantity in one and the same sampling receptacle.

Advantageously, the outlet is situated in the lower part of the second space, while the liquid channel can open into the upper part. When washing the sampling device by means of, for instance, steam supplied through the gas channel, condensate will hereby automatically drain away through the outlet because of gravity. When emptying the second space of liquid, which takes place by means of gas supplied to said space at its upper part, it is also easily avoided that the gas will stir and mix with the liquid, whereby the hot gas will not kill any bacteria in the liquid. Because of influence of the gravity on the liquid, the gas will as a piston pressing the liquid downwards in the second space towards said outlet.

BRIEF DESCRIPTION OF THE DRAWINGS

The invention will be described more closely in the following with reference to the accompanying drawing. In this.

DETAILED DESCRIPTION OF THE INVENTION

Figure 1:
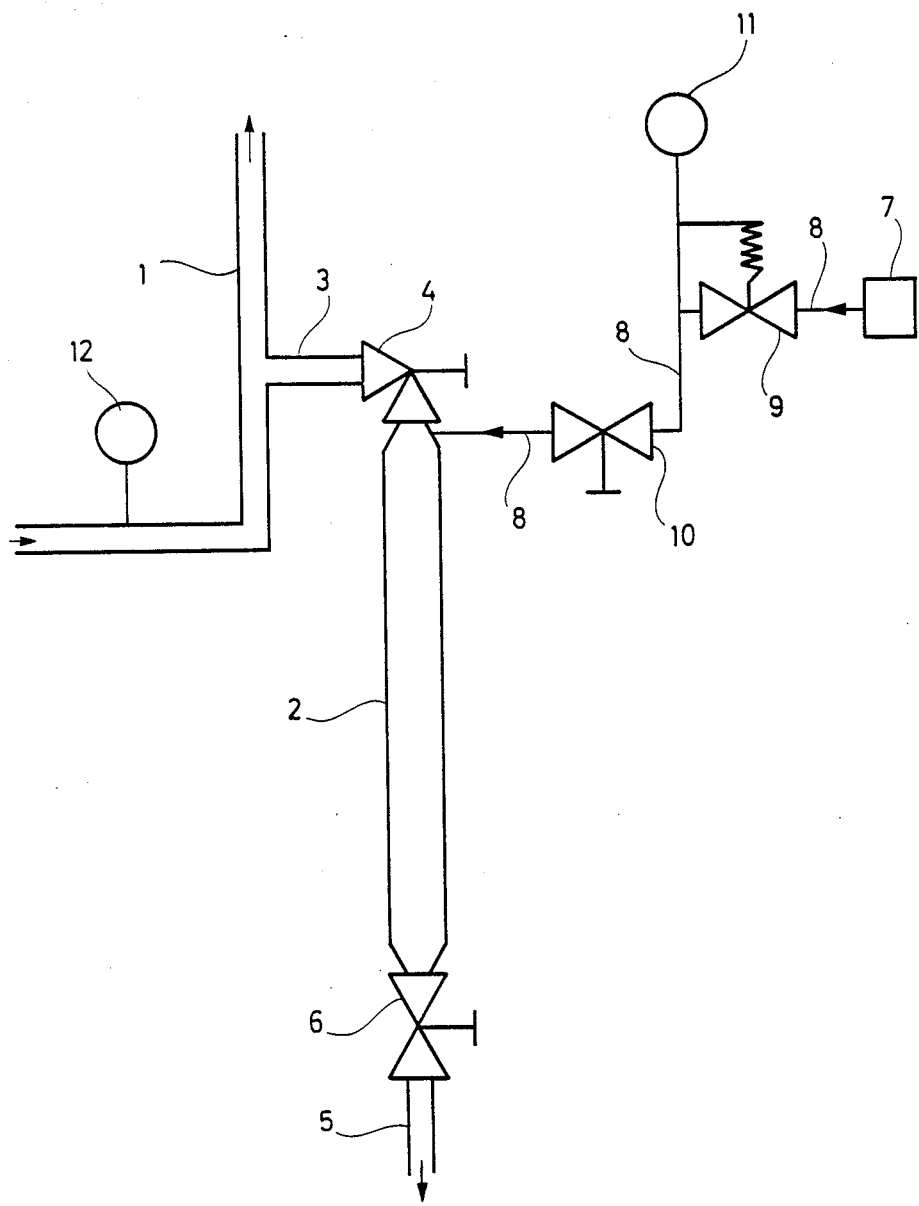
FIG. 1 shows schematically a sampling device according to the invention.

In FIG. 1, there is fundamentally shown a sampling device for aseptic transfer of a food in liquid form from a first space to a second space. The first space is here constituted by the interior of a tube conduit 1 for conveying food between, for instance, a sterilizer and an aseptic intermediate storing container, but may it also be constituted by the interior of the sterilizer or intermediate storing container. The second space is constituted by the interior of an elongated pressure vessel 2 extending vertically.

A channel 3 connects the interior of the tube conduit 1 within the interior of the pressure vessel 2. In the connection channel 3 there is a valve 4 for opening and closing the channel. The connection channel 3 opens in the upper part of the pressure vessel 2. At the lower part of the pressure vessel there is an outlet 5, which is provided with a valve 6 for opening and closing outlet 5.

A source 7 for production of gas is connected to the interior of the pressure vessel 2 in the vicinity of its upper part via a gas channel 8. In the gas channel 8 there is a pressure control valve 9, and a valve 10 for opening and closing of the gas channel, said last-mentioned valve being situated between the pressure vessel 2 and the pressure control valve 9. Two pressure gauges 11, 12 are connected to the gas channel 8 and the interior of the tube conduit 1, respectively.

The sampling device operates in the following way:

In an initial stage the liquid and gas valves 4 and 10 are closed while the outlet valve 6 is opened. First the gas source 7 is activated, after which the gas valve 10 is opened so that the gas, here in the form of steam, streams into the pressure vessel 2, air being blown out through the outlet 5 at the same time as the steam sterilizes the interior of the pressure vessel 2. Then the outlet valve 6 is closed, which means that the pressure in the pressure vessel 2 rises. By means of the pressure gauges 11, 12 and the pressure control valve 9 the pressure in the pressure vessel is adjusted so that this pressure at least amounts to substantially the pressure in the tube conduit 1. When said pressures have the same values, the gas valve 10 is closed. Now the liquid valve 4 is quickly opened, which means that liquid in the tube conduit 1 will come into contact with the steam in the pressure vessel 2. Since the temperature of the liquid is lower than the condensation temperature of the steam at said pressure, the steam begins to condense. As a result the pressure in the pressure vessel 2 decreases, which means that liquid slowly is sucked from the tube conduit 1 into the connection channel 3. When liquid begins to reach into the pressure vessel 2 the condensation takes place very quickly, the pressure vessel 2 being filled completely with liquid and with a small insignificant quantity of water from the condensed steam.

When the pressure vessel is filled the liquid valve 4 is closed, after which the outlet valve 6 is opened. Then the gas valve 10 is opened slightly, so that steam streaming into the upper part of the pressure vessel 2 presses the liquid quantity in the pressure vessel downwards and out through the outlet 5 for aseptic filling of a sterile receptacle by means of an aseptic filling device not shown. The elongated pressure vessel 2 is oriented substantially vertically to prevent as far as possible stirring of the liquid and mixing of steam into this during the emptying of the pressure vessel, since the heat steam could kill any bacteria in the sample batch, which thus would be spoiled.

Alternatively, it is also conceivable that the second space may be constituted by the interior of a sampling receptacle. In such a case this must be formed resistant to pressure variations and quick temperature changes.

Figure 2:
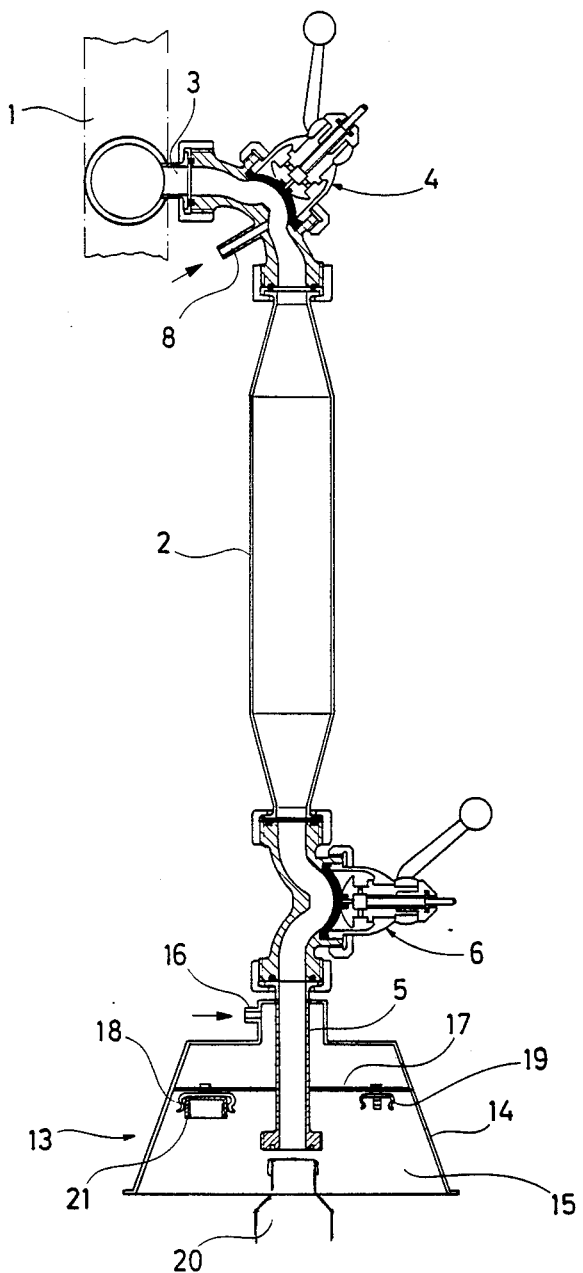
FIG. 2 shows a section through a part of a preferred embodiment of the device according to the invention.

In FIG. 2 there is shown a practical design of a part of a sampling device according to the invention provided with an aseptic filling device for sampling receptacles. Corresponding details in FIGS. 1 and 2 are provided with the same reference numerals.

In the sampling device according to FIG. 2 the valves 4 and 6 in the connection channel 3 and outlet 5, respectively, are constituted by membrane valves. Such valves are well suited for cleaning and sterilization by means of steam. In the membrane valve 4 a channel 8 for steam is connected to the outlet part of the valve in the vicinity of the valve seating. Thus the inner outlet portions of the membrane valve 4 that are most difficult of access will be safely cleaned and sterilized when supplying steam during the course of a sampling. Analogous to the device shown in FIG. 1 an elongated pressure vessel 2 is connected with its upper end to the membrane valve 4 and with its lower end to the membrane valve 6.

At the outlet 5 an aseptic filling device 13 is arranged comprising a shield 14 surrounding the outlet 5 and forming a chamber 15 with a downwards directed opening. The shield 14 is in its upper part provided with an inlet 16 for supply of a sterile gas, for instance steam, to the chamber 15. A strainer plate 17 fixed to the shield 14 divides the chamber 15 in an upper part, in which the inlet 16 for sterile gas is situated, and a lower part, in which the outlet 5 opens in downwards direction. Two holders 18 and 19 for lids to sampling receptacles are fastened to the underside of the strainer plate 17 in the lower part of the chamber 15.

The aseptic filling device 13 is used in the following way:

Steam is continuously supplied to the upper part of the chamber 15 via the inlet 16 and streams downwards to the strainer plate 17. This spreads the steam flow so that steam flows evenly into the entire lower part of the chamber 15 and leaves this via the downwards directed opening of the chamber. Hereby the chamber is kept sterile by the steam. A sterilized sampling receptacle 20, which is sealed with a lid 21, is brought with the lid portion up into the lower part of the chamber 15 and is fastened by pushing the lid 21 against the lid holder 18. (The lid holder 19 is intended for lids of smaller dimension than the lid 21). The sampling receptacle 20 is loosened from the lid 21, which is kept by the lid holder 18. Without the upper portion of the receptacle leaving the sterile environment in the lower portion of the chamber 15, the receptacle 20 is then brought to a position, in which the opening of the receptacle is in front of the opening of the outlet 5. When the receptacle 20 is in said position the membrane valve 6 is opened, after which steam is supplied to the interior of the pressure vessel 2 via the channel 8, so that the liquid amount present in the pressure vessel is pressed down into the receptacle 20. Without the upper portion of the receptacle leaving the sterile environment in the lower portion of the chamber 15, the filled receptacle 20 is brought back to the lid holder 18 and is there sealed by the lid 21, which is held by the lid holder. The receptacle 20 with its lid 21 is thereafter loosened from the lid holder 18 and is brought out of the chamber 15.

In the described exemplified embodiments of the sampling device according to FIGS. 1 and 2, the second space is constituted by the interior in a pressure vessel with unchangeable inner volume. However, alternatively it would be possible to utilize the interior of a vessel having flexible walls. When gas condenses in a vessel of the last-mentioned kind the walls in this will move towards each other so that the inner volume of the vessel decreases. However, since the liquid food is under an overpressure, the food streaming into the vessel will enlarge its inner volume back to the original size.

I claim:

1. A method of aseptically transferring liquid at a given pressure and temperature from a first space to a second space which comprises filling the second space with a sterile gas, having a condensation temperature, which, at said given pressure, is higher than the temperature of the liquid, to substantially the given pressure in the first space, bringing the first and second spaces into communication with one another, thereby causing the gas in the second space to be condensed by contact with the liquid and inducing the liquid to flow from the first space to the second space; and interrupting the communication between the first and second spaces so that the liquid in the second space is separated from the liquid remaining in the first space.

2. A sampling device for aseptic transfer of a batch of liquid at a given pressure and temperature from a first space to a second space, the second space being of a size to take up the entire batch of liquid to be transferred, comprising a channel for liquid connecting the first space with the second space, a first valve for opening and closing the channel, supply means for furnishing a sterile gas under a pressure which is, substantially, at least the given pressure, said gas having a condensation temperature which at said given pressure is higher than the temperature of the liquid, a channel for gas connecting said supply means to such second space and a second valve in said gas channel.

3. A device according to claim 2, wherein the gas channel opens into the liquid channel in the vicinity of the first valve and between the first valve and the second space.

4. A device according to claims 2 or 3, wherein that the second space is provided with an outlet and a third valve for opening and closing of the outlet.

5. A device according to claim 4, wherein the outlet is situated in the lower part of the second space.

6. A device according to claim 2, wherein the liquid channel opens into the upper part of the second space.

* * * * *